(12) United States Patent
Wu

(10) Patent No.: US 10,460,840 B2
(45) Date of Patent: Oct. 29, 2019

(54) DIAGNOSTICS-BASED HUMAN HEALTH EVALUATION

(71) Applicant: Jiangsu Huaben Health Life Science and Technology Co., Ltd., Yancheng, Jiangsu (CN)

(72) Inventor: Ben Jun Wu, Fort Erie (CA)

(73) Assignee: JIANGSU HUABEN HEALTH LIFE SCIENCE AND TECHNOLOGY CO., LTD., Jiangsu (CN)

(*) Notice: Subject to any disclaimer, the term of this patent is extended or adjusted under 35 U.S.C. 154(b) by 119 days.

(21) Appl. No.: 15/686,089

(22) Filed: Aug. 24, 2017

(65) Prior Publication Data

US 2019/0065690 A1 Feb. 28, 2019

(51) Int. Cl.
| | |
|---|---|
| *G16H 40/60* | (2018.01) |
| *A61B 5/02* | (2006.01) |
| *A61B 5/04* | (2006.01) |
| *G16H 80/00* | (2018.01) |
| *A61B 5/145* | (2006.01) |
| *A61B 5/00* | (2006.01) |

(52) U.S. Cl.
CPC .............. *G16H 40/60* (2018.01); *A61B 5/02* (2013.01); *A61B 5/04* (2013.01); *A61B 5/14* (2013.01); *A61B 5/7275* (2013.01); *A61B 5/74* (2013.01); *A61B 5/746* (2013.01); *G16H 80/00* (2018.01); *A61B 5/145* (2013.01); *A61B 5/4872* (2013.01)

(58) Field of Classification Search
CPC ..... G06F 19/3418; A61B 5/74; A61B 5/4872; A61B 5/04; A61B 5/02; A61B 5/14; G16H 50/20; G16H 50/30; G16H 50/50
See application file for complete search history.

(56) References Cited

U.S. PATENT DOCUMENTS

| | | | |
|---|---|---|---|
| 2014/0220007 A1* | 8/2014 | Glezer ................. | G01N 33/564 424/133.1 |
| 2014/0221780 A1* | 8/2014 | Goldberger .......... | A61B 5/0402 600/301 |
| 2016/0147841 A1* | 5/2016 | Gray ................. | G06F 16/24575 600/592 |
| 2016/0239624 A1* | 8/2016 | Short ..................... | G06Q 30/02 |
| 2017/0285049 A1* | 10/2017 | Schatz ............... | G01N 33/6893 |

* cited by examiner

*Primary Examiner* — Catherine M Voorhees
(74) *Attorney, Agent, or Firm* — Han IP PLLC; Andy M. Han

(57) ABSTRACT

Techniques and examples pertaining to evaluating the health condition of a patient based on a diagnostic aspect of the patient are described. A method for evaluating the health condition may involve obtaining a measurement value of the diagnostic aspect of the patient by a diagnostics measurement device. The method may also involve calculating a relative ratio by a processor communicatively coupled to the diagnostics measurement device. The processor may calculate the relative ratio by dividing the measurement value by a standard average value of the diagnostic aspect. The method may also involve the processor calculating a health deviation by subtracting a baseline value from the relative ratio. The method may also involve the processor designating a health indicator based on the health deviation, such that the health indicator serves as an indication of the health condition of the patient.

15 Claims, 3 Drawing Sheets

DIAGNOSTICS-BASED HUMAN HEALTH EVALUATION

TECHNICAL FIELD

The present disclosure generally relates to human health evaluation and, more particularly, to a method and an apparatus for evaluating human health based on results of diagnostic tests.

BACKGROUND

A diagnosis test performed on a patient in a medical environment often includes clinically examining or testing a number of diagnostic aspects of the patient. For each of the diagnostic aspects, a measurement value may be obtained and then used to evaluate a health condition of the patient at least for that particular diagnostic aspect. For example, a blood test performed on a patient may include diagnostic aspects such as a red blood cell count (RBC), a white cell count (WBC), a palette count (PLT), blood iron (i.e., amount of iron in the blood), glucose, high-density lipoprotein cholesterol (HDL-C), low-density lipoprotein cholesterol (LDL-C), triglycerides, and the like. A measurement value, e.g., a measurement value of WBC of the patient, obtained as a result of the blood test, may be used to evaluate whether the patient is healthy or not at least in the aspect of white blood cell count of the patient. The measurement value may be obtained by a diagnostics measurement device, such as a blood test device, that performs the diagnosis test on the patient.

Conventionally, the measurement value is compared to a standard upper limit and a standard lower limit of the diagnostic aspect. The standard upper limit and the standard lower limit are a maximum allowable value and a minimum allowable value, respectively, that are medically allowed for the diagnostic aspect. The patient is deemed healthy in at least the diagnostic aspect if the measurement value falls between the standard upper limit and the standard lower limit. For example, the diagnostic aspect of WBC may have a medically defined standard range of $4\text{--}10\times10^9$ counts per litter of blood, or $4\text{--}10\times10^9/L$. On the one end of the standard range is a maximum allowable value of WBC of $10\times10^9/L$, and on the other end of the standard range is a minimum allowable value of WBC of $4\times10^9/L$. That is, the standard lower limit of WBC is $4\times10^9/L$ and the standard upper limit of WBC is $10\times10^9/L$. If a patient has a WBC measurement of a value equal to or greater than the minimum allowable value and equal to or less than the maximum allowable value, e.g., $7.2\times10^9/L$, then the patient is evaluated as healthy in at least the diagnostic aspect of WBC. On the other hand, if a patient has a WBC measurement of a value less than the minimum allowable value or greater than the maximum allowable value, e.g., $2\times10^9/L$ or $12\times10^9/L$, then the patient is evaluated as unhealthy in at least the diagnostic aspect of WBC.

While the numerical form of the measurement value and the healthy range, as shown above, is technically accurate and substantially meaningful to well-trained medical practitioners, they may be less intuitive and hence difficult to comprehend for a layman. Without help from a medically-trained personnel, the patient, as a layman, may not be able to understand the significance or implications represented by the numbers regarding his or her own health condition.

Moreover, a medical fact of a developing disease, especially in an early stage of the disease, is that a measurement value of a diagnostic aspect related to the disease may already start to trend toward either the standard lower limit or the standard upper limit medically allowed for the diagnostic aspect, even though the measurement value may still be within the standard range of the diagnostic aspect (i.e., between the standard upper limit and the standard lower limit). In view of this medical fact, a few disadvantages are obvious in the aforementioned approach of evaluating a health condition of a patient. Firstly, a standard range of a diagnostic aspect is usually medically defined to be too wide (i.e., too "allowing"), which makes it difficult to raise an alarm of a disease that may still be in an early stage and developing. Secondly, since a patient is deemed healthy as long as the measurement value is within the standard range, a trend of change of the diagnostic aspect may not be tracked by a doctor or a medical practitioner. Thus, a development of a disease may be overlooked, especially when a symptom of the disease has not yet shown. A chance for preventing the symptom to develop may therefore be unintentionally missed.

In order to overcome the disadvantages regarding the conventional approach as mentioned above, and to have a better evaluation of a health condition, a method is needed to help raising an early alarm of a potentially developing disease by tracking or at least manifesting a trend of change in a measurement value of a diagnostic aspect of a patient. Meanwhile, a more intuitive representation may be developed as a health indicator to facilitate a readily understanding of the health condition from a layman's point of view.

SUMMARY

This section is for the purpose of summarizing some aspects of the present disclosure and to briefly introduce some preferred embodiments. Simplifications or omissions in this section as well as in the abstract or the title of this description may be made to avoid obscuring the purpose of this section, the abstract and the title. Such simplifications or omissions are not intended to limit the scope of the present disclosure.

According to an aspect of the present disclosure, a method for evaluating a health condition of a patient based on a diagnostic aspect of the patient is disclosed. The method involves obtaining a measurement value of the diagnostic aspect of the patient. The measurement value is obtained by a diagnostics measurement device. The method also involves calculating a relative ratio by a processor that is communicatively coupled to the diagnostics measurement device. The processor calculates the relative ratio by dividing the measurement value by a standard average value of the diagnostic aspect. The standard average value is an arithmetic mean of a standard upper limit and a standard lower limit that are medically defined for the diagnostic aspect. The method further involves calculating a health deviation by the processor. The processor may calculate the health deviation by subtracting a baseline value from the relative ratio. The baseline value is an arithmetic sum of a medium value, a variation upper limit, a variation lower limit, and a tier size. The method also involves designating a health indicator by the processor. The processor designates the health indicator based on the health deviation, and the health indicator indicates the health condition of the patient.

In some embodiments, the diagnostics measurement device is a blood test device, and the measurement value is a result of a blood test performed by the blood test device on the patient. In some embodiments, the diagnostic aspect includes a RBC, a WBC or a PLT. In some embodiments, the health indicator, as designated by the processor, is a rounded integer of a ratio of the health deviation to the tier size. A higher absolute value of the rounded integer indicates that the health condition of the patient is less ideal than a lower absolute value of the rounded integer. When a value of the health indicator is less than a healthy low range or greater than a healthy high range, the health indicator indicates the health condition of the patient to be less than ideal. The healthy low range is typically between −3 and −6, and the healthy high range is typically between +1 and +3.

According to another aspect of the present disclosure, an apparatus capable of evaluating a health condition of a patient is disclosed. The apparatus includes a memory capable of storing one or more sets of instructions and one or more standard values, a baseline value and a standard average value of a diagnostic aspect. The apparatus also includes a processor coupled to execute the one or more sets of instructions stored in the memory such that, upon executing the one or more sets of instructions, the processor may receive a measurement value of the diagnostic aspect of the patient. Also, the processor may calculate a relative ratio by dividing the measurement value by the standard average value. In addition, the processor may calculate a health deviation by subtracting the baseline value from the relative ratio. Finally, the processor may, based on the health deviation, designate a health indicator that indicates the health condition of the patient.

In some embodiments, the apparatus also includes one or more diagnostics measurement devices, such as a blood test device. The blood test device is capable of performing a blood test on the patient. Specifically, the measurement value is a result of the blood test performed by the blood test device on the patient, and the standard average value is an arithmetic mean of a standard upper limit and a standard lower limit. The standard upper limit and the standard lower limit are, respectively, a maximum allowable value and a minimum allowable value that are medically allowed for the diagnostic aspect.

In some embodiments, the memory of the apparatus is further capable of storing a tier size. Also, the health indicator is a rounded integer of a ratio of the health deviation to the tier size. In some embodiments, the processor of the apparatus includes a tensor processing unit (TPU) that is capable of developing artificial intelligence (AI) of medical diagnosis. Consequently, the processor is capable of medically diagnosing the patient based on the health indicator with the AI.

BRIEF DESCRIPTION OF THE DRAWINGS

These and other features, aspects, and advantages of the present disclosure will become better understood with regard to the following description, appended claims, and accompanying drawings where:

DETAILED DESCRIPTION OF THE PREFERRED EMBODIMENTS

The detailed description of the present disclosure is presented largely in terms of procedures, steps, logic blocks, processing, or other symbolic representations that directly or indirectly resemble the operations of devices or systems contemplated in the present disclosure. These descriptions and representations are typically used by those skilled in the art to most effectively convey the substance of their work to others skilled in the art.

Reference herein to "one embodiment" or "an embodiment" means that a particular feature, structure, or characteristic described in connection with the embodiment can be comprised in at least one embodiment of the present disclosure. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams or the use of sequence numbers representing one or more embodiments of the present disclosure do not inherently indicate any particular order nor imply any limitations in the present disclosure.

To make the above objects, features and advantages of the present disclosure more obvious and easier to understand, the present disclosure is further described in detail below using various embodiments.

Figure 1:
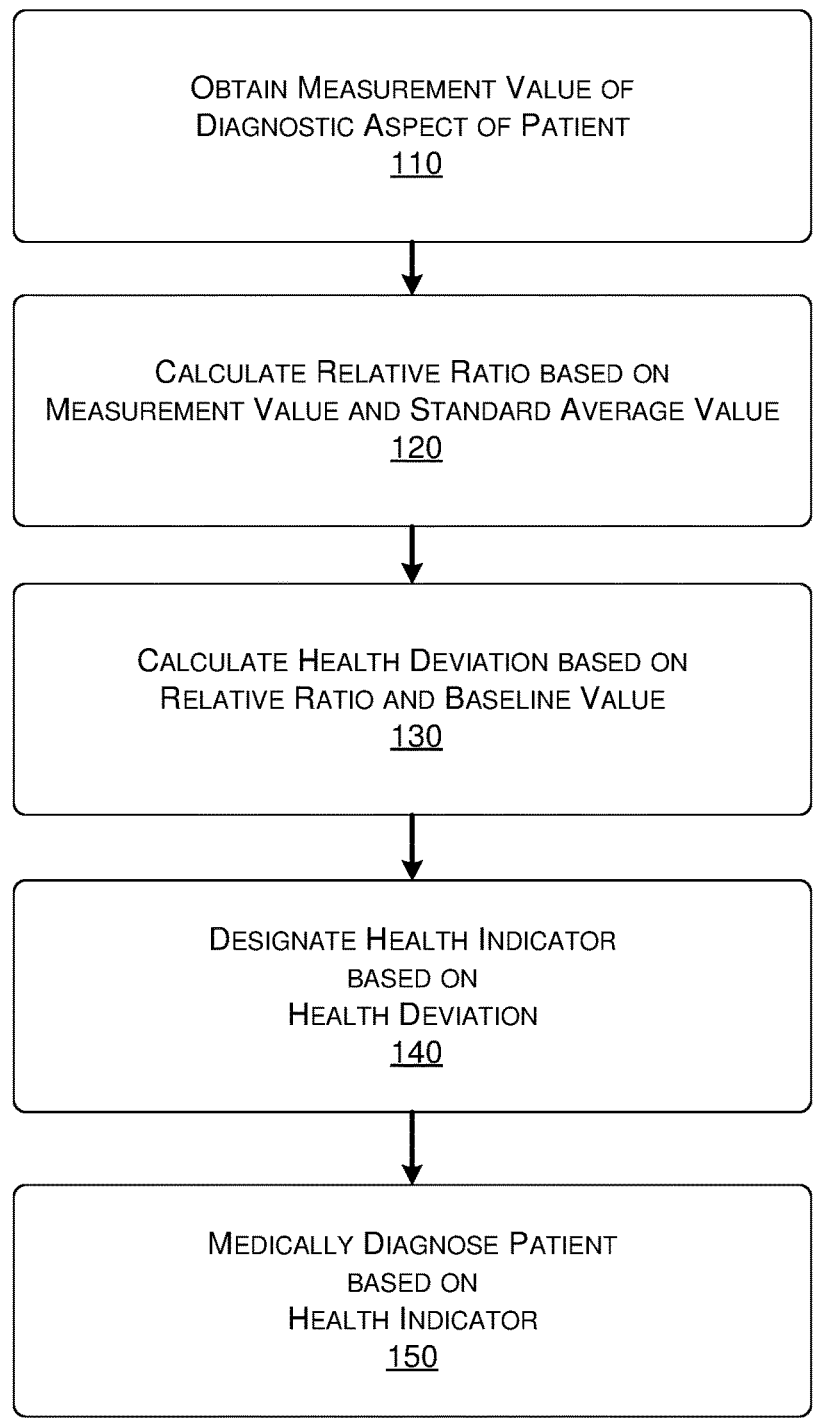
FIG. 1 is a flowchart depicting an example process in accordance with an embodiment of the present disclosure.

FIG. 1 illustrates an example process 100, in accordance with the present disclosure, for evaluating a health condition of a patient based on a diagnostic aspect of the patient. Process 100 may include one or more operations, actions, or functions shown as blocks such as 110, 120, 130, 140 and 150. Although illustrated as discrete blocks, various blocks of process 100 may be divided into additional blocks, combined into fewer blocks, or eliminated, depending on the desired implementation. Process 100 may begin with block 110.

At 110, process 100 may involve obtaining a measurement value of the diagnostic aspect of the patient by a diagnostics measurement device. For example, a blood test device (i.e., the diagnostics measurement device) may perform a blood test on the patient to examine blood iron (i.e. the diagnostic aspect) of the patient. The blood test device may report or otherwise obtain a measurement value of 4.2 micro moles per litter (i.e., 4.2 umol/L, or $4.2 \times 10^{-6}$ moles per litter of blood) as a result of the blood test. That is, the blood test device may obtain the measurement value of 4.2 umol/L as the amount of iron in the blood of the patient. Process 100 may proceed from 110 to 120.

At 120, process 100 may involve calculating a relative ratio by dividing the measurement value obtained at 110 by a standard average value of the diagnostic aspect. The standard average value of the aspect may be found by taking an arithmetic mean of a standard upper limit and a standard lower limit. The standard upper and lower limits may be medically defined as a standard for the diagnostic aspect, and may respectively represent a maximum allowable value and a minimum allowable value medically allowed for the diagnostic aspect. In addition, the standard upper and lower limits may be universally applicable to all patients for the diagnostic aspect. For example, a diagnostic aspect, blood iron, may have a standard lower limit of 5.2 umol/L, and a standard upper limit of 26.6 umol/L Namely, it is medically defined that a maximum allowable value of blood iron is 26.6 umol/L, while a minimum allowable value of blood iron is 5.2 umol/L. Therefore, the standard average value may be found as an arithmetic mean of 5.2 umol/L and 26.6 umol/L, namely, 15.9 umol/L. The relative ratio may subsequently be found by dividing the measurement value by the standard average value of the diagnostic aspect. That is, the relative ratio may be calculated as 4.2 umol/L divided by 15.9 umol/L, or 0.264. A processor communicatively coupled to the diagnostics measurement device may be used to calculate the relative ratio. Process 100 may proceed from 120 to 130.

At 130, process 100 may involve the processor calculating a health deviation by subtracting a baseline value from the relative ratio. The baseline value may consist of four parts: a medium value, a variation upper limit, a variation lower limit, and a tier size. Specifically, the baseline value is an arithmetic sum of the four parts. In some embodiments, value of each of the four parts may be specific to the diagnostic aspect of which the measurement is obtained at block 110. Typically, the medium value is unity, or 1, and the variation upper limit and the variation lower limit are equal in respective absolute values but opposite in respective signs. Centered by the medium value, a "healthy range" of the relative ratio may be defined by (medium value+variation lower limit) on a low side of the range and (medium value+variation upper limit) on a high side of the range. The healthy range represents a range of the relative ratio in which the health condition of the patient, at least in the diagnostic aspect, is considered "perfect", or "completely healthy". A relative ratio having a value outside of the healthy range may mean that the health condition of the patient, at least in the diagnostic aspect, is less than perfect, or not completely healthy. A parameter, health deviation, may be used to characterize or otherwise represent how far away the health condition is from "perfect" or "completely healthy". The tier size is related to how coarse or fine a scale may be used to represent the health deviation in various tier values.

Continuing with the blood test example used above in 110 and 120 of process 100, 130 may be exemplified as follows. For example, the variation upper limit and the variation lower limit may be +9% and −9%, respectively. The tier size may be 10%. Therefore, the baseline value would be 1+9%−9%+10%=1.1. Therefore, the health deviation may be calculated as the relative ratio subtracted by the baseline value, or 0.264−1.1=−0.836. Process 100 may proceed from 130 to 140.

At 140, process 100 may involve the processor designating a health indicator based on the health deviation calculated in 130. The health indicator may indicate the health condition of the patient in at least the diagnostic aspect. Specifically, the health indicator may be a rounded integer of a ratio of the health deviation to the tier size. That is, the health indicator may be seen as the health deviation scaled or otherwise normalized to the tier size. The ratio may be rounded to an integer if the ratio is less than the integer plus 0.5, or if the ratio is equal or larger than the integer minus 0.5. With the tier size being 10% in the example and the health deviation of −0.836 as calculated in 130, the ratio may be calculated as −0.836/10%=−8.36. Therefore, process 100 may involve the processor designating a rounded integer of −8 (i.e., −8.36 is rounded to integer −8) as the health indicator indicating the health condition of the patient in the diagnostic aspect of blood iron. As a signed integer, the health indicator serves as an intuitive and comprehensive means that indicates the health condition of the patient in at least the diagnostic aspect.

The health indicator may be compared to a healthy low range and/or a healthy high range to reveal how far away the health condition of the patient is from "perfect" or "completely healthy". Specifically, the health indicator may indicate the health condition to be less than ideal when a value of the health indicator is less than a healthy low range or greater than a healthy high range. For example, the healthy low range may be between −3 and −6, and the healthy high range may be between +1 and +3. Apparently, the health indicator of −8 indicates that the health condition is less than ideal, as the value −8 is less than the healthy low range of −3~−6.

Moreover, an absolute value of the rounded integer may indicate the health condition of the patient. That is, a higher absolute value of the rounded integer may indicate the health condition of the patient to be less ideal than a lower absolute value of the rounded integer. On the other hand, a lower absolute value of the rounded integer may indicate the health condition of the patient to be more ideal than a higher absolute value of the rounded integer. Continuing with the blood test example, the health indicator is currently designated as −8, which has an absolute value of 8. Assuming that the patient subsequently undergoes some treatment for two weeks, and after the two-week treatment a new measurement value of the blood iron is obtained, at block 110 of process 100, as 7.0 umol/L. The standard average value of blood iron is irrelevant to the new measurement value and remains 15.9 umol/L. Thus, the processor would calculate, at block 120 of process 100, a new relative ratio of 7.0/15.9=0.440. With the baseline value remaining 1.1, the processor would calculate, at block 130 of process 100, a new health deviation to be 0.440−1.1=−0.660. The processor would then designate, at block 140 of process 100, a rounded integer −7 as a new health indicator based on the new health deviation. Apparently, the health condition of the patient based on the blood iron is still less than ideal, as the new health indicator, −7 is still less than the healthy low range of −3~−6. Nevertheless, the absolute value of the health indicator after the two-week treatment, 7, is less than the absolute value of the health indicator prior to the two-week treatment, 8, which indicates the patient has become healthier (i.e., the health condition of the patient has become more ideal) after the treatment. Namely, the decrease in the absolute value of the health indicator indicates that the treatment applied to the patient during the two weeks has improved the health condition of the patient in at least the diagnostic aspect of blood iron. Process 100 may proceed from 140 to 150.

At 150, process 100 may involve the processor medically diagnosing the patient based on the health indicator designated in block 140. Specifically, the processor may include a TPU that is capable for developing AI of medical diagnosis. Based on the health indicator designated in block 140, the processor may medically diagnose the patient with a possible disease, as well as a treat plan for the disease. With the TPU, the processor may exercise a self-training capability of the AI to improve or refine the medical diagnosis and the treatment plan.

Although process 100 of FIG. 1 is applied to the diagnostic aspect of blood iron, process 100 may be applicable to other diagnostic aspects of the blood test, such as RBC, WBC, PLT, glucose, HDL-C, LDL-C and one or more triglycerides.

Figure 2:
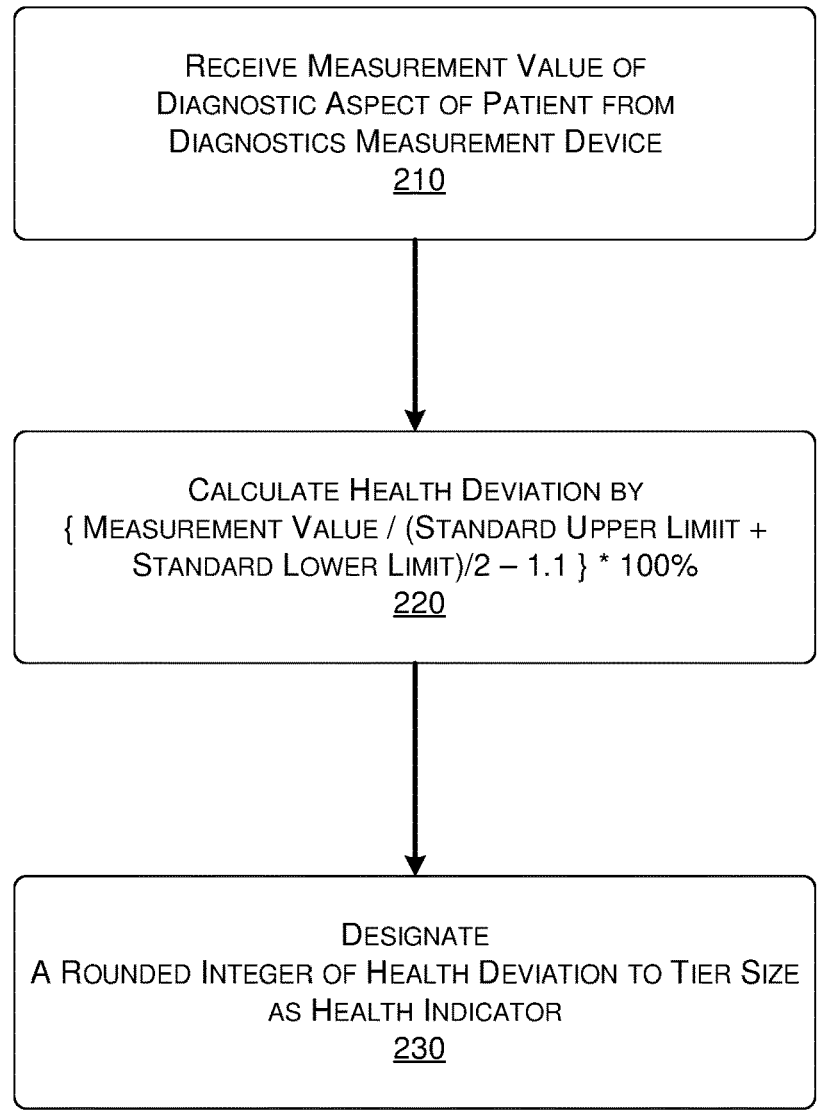
FIG. 2 is a flowchart depicting another example process in accordance with an embodiment of the present disclosure.

FIG. 2 illustrates an example process 200, in accordance with the present disclosure, for evaluating a health condition of a patient based on a diagnostic aspect of the patient. Process 200 may include one or more operations, actions, or functions shown as blocks such as 210, 220 and 230. Although illustrated as discrete blocks, various blocks of process 200 may be divided into additional blocks, combined into fewer blocks, or eliminated, depending on the desired implementation. Process 200 may begin with block 210.

At 210, process 200 may involve a processor receiving a measurement value of a diagnostic aspect of the patient from a diagnostics measurement device. The measurement value may be a result of a medical test performed by the diagnostics measurement device on the patient. For example, the diagnostics measurement device may be a blood test device, and the medical test may be a blood test performed by the blood test device on the patient. The diagnostic aspect of the patient may be a WBC of the patient, and the measurement value, reported by the blood test device as a result of the blood test, may be $14.7 \times 10^9$ counts per litter of blood. Process 200 may proceed from 210 to 220.

At 220, process 200 may involve the processor calculating a health deviation of the diagnostic aspect of the patient using the following equation:

health deviation={measurement value/[(standard upper limit+standard lower limit)/2]−1.1}*100%.

The standard upper limit and the standard lower limit are respectively a maximum allowable value and a minimum allowable value medically allowed for the diagnostic aspect. For example, the maximum allowable value that is medically allowed for WBC is $10 \times 10^9$ counts per litter of blood, whereas the minimum allowable value that is medically allowed for WBC is $4 \times 10^9$ counts per litter of blood. Therefore, the standard upper limit to be applied in the equation above is $10 \times 10^9$/L, whereas the standard lower limit to be applied in the equation above is $4 \times 10^9$/L. The processor may subsequently calculate the health deviation as $\{14.7 \times 10^9/[(10 \times 10^9 + 4 \times 10^9)/2] - 1.1\} \times 100\% = 1.0$. Process 200 may proceed from 220 to 230.

At 230, process 200 may involve the processor designating a health indicator based on the health deviation. Specifically, the heath indicator may be a rounded integer of a ratio of the health deviation, as calculated in block 220, to a tier size. The tier size is related to how coarse or fine a scale may be used to represent the health deviation in various tier values. The ratio may be rounded to an integer if the ratio is less than the integer plus 0.5, or if the ratio is equal or larger than the integer minus 0.5. The health indicator may indicate or otherwise represent the health condition of the patient at least in the diagnostic aspect. For example, at block 230, the tier size may be 10%, and thus the heath indicator would be designated as a rounded integer of 1.0/10%, which is +10.

Similar to the health indicator of process 100, the health indicator of process 200 may be compared to a healthy low range and/or a healthy high range to reveal how far away the health condition of the patient is from "perfect" or "completely healthy". Specifically, the health indicator may indicate the health condition to be less than ideal when a value of the health indicator is less than a healthy low range or greater than a healthy high range. For example, the healthy low range may be between −3 and −6, and the healthy high range may be between +1 and +3. Apparently, the health indicator of +10, as designated in block 230 of process 200, indicates that the health condition is less than ideal, as the value +10 is greater than the healthy high range of +1~+3.

Also similar to the health indicator of process 100, the absolute value of the health indicator of process 200 may indicate the health condition of the patient. That is, a higher absolute value of the rounded integer may indicate the health condition of the patient to be less ideal than a lower absolute value of the rounded integer. On the other hand, a lower absolute value of the rounded integer may indicate the health condition of the patient to be more ideal than a higher absolute value of the rounded integer. Assuming that the patient subsequently undergoes some treatment for a certain period of time, and after the treatment a new measurement value of WBC is received, at block 210 of process 200, as $11.0 \times 10^9$/L. The health deviation after the treatment may be calculated, at block 220 of process 200, as $\{11.0 \times 10^9/[(10 \times 10^9 + 4 \times 10^9)/2] - 1.1\} \times 100\% = 0.471$. With the 10% tier size, the processor would then designate, at block 230 of process 200, a rounded integer +5 as a health indicator after the treatment based on the health deviation after the treatment. Apparently, the health condition of the patient based on the WBC is still less than ideal, as the new health indicator, +5 is still greater than the healthy high range of +1~+3. Nevertheless, the absolute value of the health indicator after the treatment, 5, is less than the absolute value of the health indicator prior to the treatment, 10, which indicates that the patient has become healthier (i.e., the health condition of the patient has become more ideal) after the treatment. Namely, the decrease in the absolute value of the health indicator indicates that the treatment applied to the patient has improved the health condition of the patient in at least the diagnostic aspect of WBC.

Although process 200 of FIG. 2 is applied to the diagnostic aspect of WBC, process 200 may be applicable to other diagnostic aspects of the blood test, such as RBC, PLT, blood iron, glucose, HDL-C, LDL-C and one or more triglycerides.

Figure 3:
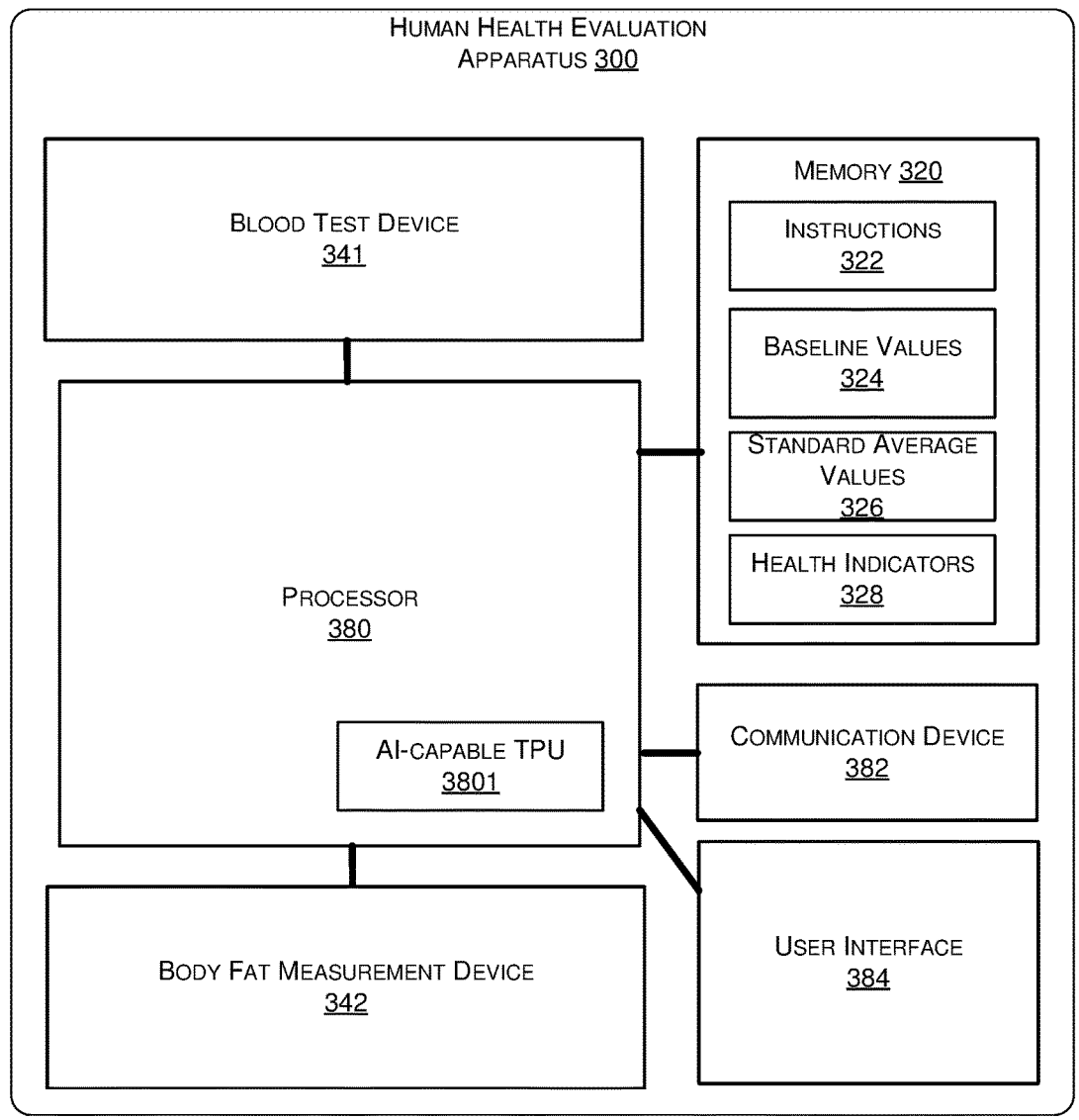
FIG. 3 is a block diagram depicting an example apparatus in accordance with an embodiment of the present disclosure.

FIG. 3 illustrates an example apparatus, i.e., human health evaluation apparatus 300, that is capable of evaluating a health condition of a patient based on one or more diagnostic aspects of the patient, in accordance with an embodiment of the present disclosure. Apparatus 300 may perform various functions related to techniques, methods and systems described herein, including those described above regarding process 100 of FIG. 1 and process 200 of FIG. 2. Apparatus 300 may include at least some of the components illustrated in FIG. 3.

Referring to FIG. 3, human health evaluation apparatus 300 may include processor 380 and memory 320. Memory 320 may store, for each diagnostic aspect, a respective baseline value 324 used in block 130 of process 100 of FIG. 1. Memory 320 may also store a medium value, a variation upper limit, a variation lower limit, and a tier size that may be used by processor 380 to compute baseline value 324 (e.g., as described above regarding block 130 of process 100 of FIG. 1) before baseline value 324 is stored in memory 320. Memory 320 may also store, for each diagnostic aspect, a respective standard average value 326 used in block 120 of process 100 of FIG. 1. Alternatively or additionally, memory 320 may also store a standard upper limit and standard lower limit used in block 120 of process 100 of FIG. 1 and in block 220 of process 200 of FIG. 2. Memory 320 may also store one or more sets of instructions 322 for processor 380 to execute and perform the various obtaining, calculating and designating operations as described above in the present disclosure, including those performed in process 100 of FIG. 1 and process 200 of FIG. 2. For example, processor 380 may execute one or more sets of instructions 322 to receive a measurement value of a diagnostic aspect of the patient from a diagnostics measurement device coupled to processor 380, to calculate a relative ratio by dividing the measurement value by a standard average value 326 specific to the diagnostic aspect, to calculate a health deviation by subtracting a baseline value 324 from the relative ratio, and to designate a health indicator 328 based on the health deviation. In some embodiments, memory 320 may also store the health indicator 328.

In some embodiments, apparatus 300 may include one or more diagnostics measurement devices, including the diagnostics measurement device from which processor 380 receives the measurement value from. For example, apparatus 300 may include a blood test device 341, from which processor 380 may receive a measurement value of a diagnostic aspect of the patient such as RBC, WBC, PLT, blood iron, glucose, HDL-C and LDL-C. As another example, apparatus 300 may include a body fat measurement device 342, from which processor 380 may receive a measurement value of a diagnostic aspect of the patient such as body fat percentage and/or muscle percentage.

In some embodiments, apparatus 300 may further include a communication device 382 that is capable of wirelessly transmitting and receiving data. For example, communication device 382 may be used by processor 380 to remotely access a data server and receive standard upper and lower limits that may be used by processor 380 to calculate a standard average value 326 stored in memory 320. Communication device 382 may also be used by processor 380 to transmit health indicators 328, as designated by processor 380, to a medical practitioner located at a remote location. In some embodiments, apparatus 300 may additionally include a user interface 384 for communicating with the patient or a local medical practitioner.

In some embodiments, processor 380 of apparatus 300 may include a TPU 3801 that is capable for developing AI of medical diagnosis. TPU 3801 may exercise a self-training capability of the AI using data stored in memory 320 and feedback from a human medical practitioner to refine or update standard average values 326 and improve an algorithm of designating health indicators 328.

The present disclosure has been described in sufficient details with a certain degree of particularity. It is understood to those skilled in the art that the present disclosure of embodiments has been made by way of examples only and that numerous changes in the arrangement and combination of parts may be resorted without departing from the spirit and scope of the present disclosure as claimed. Accordingly, the scope of the present disclosure is defined by the appended claims rather than the foregoing description of embodiments.

ADDITIONAL NOTES

The herein-described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Further, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Moreover, it will be understood by those skilled in the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various implementations of the present disclosure have been described herein for purposes of illustration, and that various modifications may be made without departing from the scope and spirit of the present disclosure. Accordingly, the various implementations disclosed herein are not intended to be limiting, with the true scope and spirit being indicated by the following claims.

What is claimed is:

1. A method of evaluating a health condition of a patient based on a diagnostic aspect of the patient, comprising:

obtaining, by a diagnostics measurement device, a measurement value of the diagnostic aspect of the patient;

calculating, by a processor communicatively coupled to the diagnostics measurement device, a relative ratio by dividing the measurement value by a standard average value of the diagnostic aspect;

calculating, by the processor, a health deviation by subtracting a baseline value from the relative ratio; and designating, by the processor, a health indicator based on the health deviation, the health indicator indicating the health condition of the patient, wherein:
the diagnostics measurement device comprises a blood test device,
the measurement value is a result of a blood test performed by the blood test device on the patient,
the standard average value comprises an arithmetic mean of a standard upper limit and a standard lower limit that are medically defined for the diagnostic aspect,
the baseline value comprises an arithmetic sum of a medium value, a variation upper limit, a variation lower limit, and a tier size, and
the health indicator is a rounded integer of a ratio of the health deviation to the tier size.

2. The method of claim 1, wherein:
the medium value equals to 1,
the variation upper limit and the variation lower limit are equal in respective absolute values and opposite in respective signs, and
the tier size is 10%.

3. The method of claim 2, wherein the variation upper limit is +9% and the variation lower limit is −9%.

4. The method of claim 1, wherein the diagnostic aspect comprises a red blood cell count (RBC), a white blood cell count (WBC), or a platelet count (PLT).

5. The method of claim 1, wherein a higher absolute value of the rounded integer indicates the health condition of the patient to be less ideal than a lower absolute value of the rounded integer.

6. The method of claim 1, wherein:
the health indicator indicates the health condition of the patient to be less than ideal when a value of the health indicator is less than a healthy low range or greater than a healthy high range,
the healthy low range is between −3 and −6, and
the healthy high range is between +1 and +3.

7. The method of claim 1, wherein the rounded integer equals to the ratio rounded to a first integer in response to the ratio being less than the first integer plus 0.5, and wherein the rounded integer equals to the ratio rounded to a second integer in response to the ratio equal to or larger than the second integer minus 0.5.

8. An apparatus capable of evaluating a health condition of a patient, comprising:
a blood test device capable of performing a blood test on the patient;
a memory capable of storing one or more sets of instructions, a baseline value, a tier size, and a standard average value of a diagnostic aspect; and
a processor coupled to execute the one or more sets of instructions stored in the memory so that, upon executing the one or more sets of instructions, the processor performs operations comprising:
receiving a measurement value of the diagnostic aspect of the patient;
calculating a relative ratio by dividing the measurement value by the standard average value;
calculating a health deviation by subtracting the baseline value from the relative ratio; and
designating a health indicator based on the health deviation, the health indicator indicating the health condition of the patient, wherein:
the measurement value is a result of the blood test performed by the blood test device on the patient,
the standard average value comprises an arithmetic mean of a standard upper limit and a standard lower limit, the standard upper limit and the standard lower limit being respectively a maximum allowable value and a minimum allowable value that are medically allowed for the diagnostic aspect, and
the health indicator is a rounded integer of a ratio of the health deviation to the tier size.

9. The apparatus of claim 8, wherein a higher absolute value of the rounded integer indicates the health condition of the patient to be less ideal than a lower absolute value of the rounded integer.

10. The apparatus of claim 8, wherein the processor comprises a tensor processing unit (TPU) capable of developing artificial intelligence (AI) of medical diagnosis, and wherein the operations further comprise:
medically diagnosing the patient based on the health indicator with the AI.

11. A method of evaluating a health condition of a patient based on a diagnostic aspect of the patient, comprising:
receiving, by a processor from a diagnostics measurement device, a measurement value of the diagnostic aspect of the patient as a result of a medical test performed by the diagnostics measurement device on the patient,
calculating, by the processor, a health deviation of the diagnostic aspect of the patient using an equation as follows:

$$\text{health deviation} = \{\text{measurement value}/[(\text{standard upper limit} + \text{standard lower limit})/2] - 1.1\} * 100\%; \text{ and}$$

designating a health indicator based on the health deviation, the health indicator indicating the health condition of the patient, wherein:
the standard upper limit and the standard lower limit are respectively a maximum allowable value and a minimum allowable value medically allowed for the diagnostic aspect, and
the medical test comprises a blood test, and wherein the diagnostic aspect comprises a red blood cell count (RBC), a white blood cell count (WBC), or a platelet count (PLT).

12. The method of claim 11, wherein the designating of the health indicator based on the health deviation comprises designating as the health indicator a rounded integer of a ratio of the health deviation to a tier size.

13. The method of claim 12, wherein a higher absolute value of the rounded integer indicates the health condition of the patient to be less ideal than a lower absolute value of the rounded integer.

14. The method of claim 11, wherein the health indicator indicates the health condition of the patient to be less than ideal when a value of the health indicator is less than a healthy low range or greater than a healthy high range.

15. The method of claim 14, wherein the healthy low range is between −3 and −6, and wherein the healthy high range is between +1 and +3.

* * * * *